United States Patent [19]

Everly et al.

[11] Patent Number: 4,532,356

[45] Date of Patent: Jul. 30, 1985

[54] CHEMICAL PROCESS

[75] Inventors: Charles R. Everly; Jerry M. Roper, both of Baton Rouge, La.

[73] Assignee: Ethyl Corporation, Richmond, Va.

[21] Appl. No.: 552,284

[22] Filed: Nov. 16, 1983

[51] Int. Cl.³ .............................................. C07C 45/61
[52] U.S. Cl. ..................................... 568/315; 568/308
[58] Field of Search ................................. 568/315, 308

[56] References Cited

U.S. PATENT DOCUMENTS

| | | | |
|---|---|---|---|
| 3,678,095 | 7/1972 | Dexter et al. | 568/308 |
| 3,989,738 | 11/1976 | Kline | 568/308 |
| 4,060,556 | 11/1977 | Parker | 568/315 |
| 4,177,213 | 12/1979 | Schmidt | 568/315 |
| 4,186,151 | 1/1980 | Kubota et al. | 568/315 |
| 4,208,425 | 6/1980 | Diana | 568/315 |
| 4,456,770 | 6/1984 | Everly et al. | 568/315 |
| 4,456,771 | 6/1984 | Everly et al. | 568/315 |

*Primary Examiner*—James H. Reamer
*Attorney, Agent, or Firm*—Donald L. Johnson; John F. Sieberth; Patricia J. Hogan

[57] ABSTRACT

Novel bis(3',5'-mono or dihydrocarbyl-4'-hydroxybenzyl)-1,3-diketones are prepared by reacting a (3',5'-mono or dihydrocarbyl-4'-hydroxybenzyl)-1,3-diketone with an N,N-dihydrocarbyl-2,6-mono or dihydrocarbyl-4-aminomethylphenol and an alkyl halide in the presence of an alkaline earth metal halide. The products are useful as antioxidants.

32 Claims, No Drawings

CHEMICAL PROCESS

TECHNICAL FIELD

This invention relates to novel and useful bis(3′,5′-mono or dihydrocarbyl-4′-hydroxybenzyl)-1,3-diketones and the preparation and uses thereof as antoxidants for oxidizable organic materials when such materials are exposed to oxidative, degradative conditions.

THE INVENTION

The materials of this invention are prepared by reacting a (3′,5′-mono or dihydrocarbyl-4′-hydroxybenzyl)-1,3-diketone with an N,N-dihydrocarbyl-2,6-mono or dihydrocarbyl-4-aminomethylphenol and an alkyl halide in the presence of an alkaline earth metal halide. Thus, in one embodiment of the invention, there is provided a novel process for the preparation of bis(3′,5′-mono or dihydrocarbyl-4′-hydroxybenzyl)-1,3-diketones which comprises reacting a (3′,5′-mono or dihydrocarbyl-4′-hydroxybenzyl)-1,3-diketone with an N,N-dihydrocarbyl-2,6-mono or dihydrocarbyl-4-aminomethylphenol and an alkyl halide in the presence of an alkaline earth metal halide.

The process can be illustrated schematically by the following equations. Compounds having the general formula:

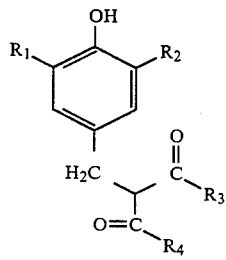

(I)

are reacted with compounds having the general formula:

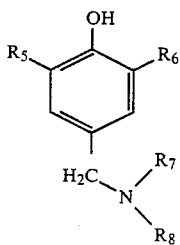

(II)

and an alkyl halide of the general formula:

$R_9X$  (III)

in the presence of an alkaline earth metal halide to yield a bis(3′,5′-mono or dihydrocarbyl-4′-hydroxybenzyl)-1,3-diketone having the structural formula:

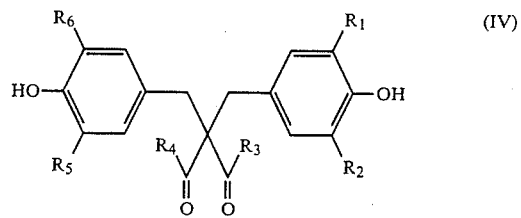

In the structural formulas above, $R_1$, $R_2$, $R_5$ and $R_6$, are the same or different and are hydrogen or hydrocarbyl radicals, preferably alkyl, aralkyl or cycloalkyl radicals having from 1 to about 20 carbon atoms each, and more preferably from 3 to 8 carbon atoms each with the provision that at least one of $R_1$ or $R_2$ and $R_5$ or $R_6$ must be other than hydrogen, $R_3$, $R_4$, $R_7$ and $R_8$ are the same or different and are hydrocarbyl radicals, preferably alkyl, aralkyl or cycloalkyl radicals having from 1 to about 20 carbon atoms, more preferably from 3 to 8 carbon atoms each, and $R_9$ is a linear or branched alkyl radical having from 1 to about 20 carbon atoms and X is bromine, chlorine or iodine.

Thus, in one embodiment of the present invention, there is provided a process for the preparation of bis(3′,5-mono or dihydrocarbyl-4′-hydroxybenzyl)-1,3-diketones having the general formula:

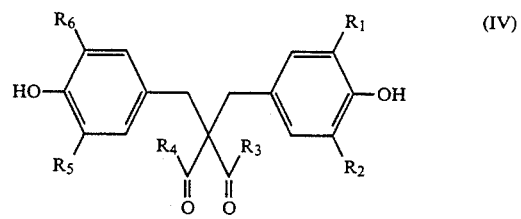

which comprises reacting a (3′,5′-mono or dihydrocarbyl-4′-hydroxybenzyl)-1,3-diketone having the general formula (I) with an N,N-dihydrocarbyl-2,6-mono or dihydrocarbyl-4-aminomethylphenol of the general formula (II) and an alkyl halide of the formula $R_9X$ (III) in the presence of an alkaline earth metal halide wherein in the structural formulas above $R_1$, $R_2$, $R_5$ and $R_6$, are the same or different and are hydrogen or hydrocarbyl radicals, preferably alkyl, aralkyl or cycloalkyl radicals having from 1 to about 20 carbon atoms each, and more preferably from 3 to 8 carbon atoms each with the provision that at least one of $R_1$ or $R_2$ and $R_5$ or $R_6$ must be other than hydrogen, $R_3$, $R_4$, $R_7$ and $R_8$ are the same or different and are hydrocarbyl radicals preferably alkyl, aralkyl or cycloalkyl radicals having from 1 to about 20 carbon atoms, more preferably from 3 to 8 carbon atoms each, and $R_9$ is a linear or branched alkyl radical having from 1 to about 20 carbon atoms and X is bromine, chlorine or iodine.

Representative examples of radicals described above are secondary radicals such as secondary butyl, secondary amyl, secondary octyl; tertiary radicals such as tertiary butyl, tertiary hexyl and tertiary decyl; alkyl radicals such as methyl, ethyl, propyl, butyl, nonyl, decyl, tetradecyl, hexadecyl, nonadecyl; aralkyl radicals such as methylphenyl and pentylphenyl, and cycloalkyl radicals such as cyclopentyl, cyclohexyl and cycloheptyl radicals.

Representative examples of Group I benzylated 1,3-diketone compounds include:

3-(3′,5′-di-t-butyl-4′-hydroxybenzyl)-2,4-pentanedione,
3-(3′-methyl-5′-isopropyl-4′-hydroxybenzyl)-2,4-pentanedione,
3-(3′-methyl-5′-t-butyl-4′-hydroxybenzyl)-2,4-pentanedione,
3-(3′,5′-diisopropyl-4′-hydroxybenzyl)-2,4-pentanedione,
3-(3′-sec-butyl-4′-hydroxybenzyl)-2,4-pentanedione,
3-(3′-isopropyl-4′-hydroxybenzyl)-2,4-pentanedione,
3-(3′-t-butyl-4′-hydroxybenzyl)-2,4-pentanedione,
3-(3′-ethyl-5′-methyl-4′-hydroxybenzyl)-2,4-heptanedione,
5-(3′,5′-dioctyl-4′-hydroxybenzyl)-4,6-nonanedione,
4-(3′-t-butyl-5′-heptyl-4′-hydroxybenzyl)-2,6-dimethyl-3,5-heptanedione,
3-(3′,5′-dioctyl-4′-hydroxybenzyl)-2,4-decanedione
3-(3′,5′-dioctyl-4′-hydroxybenzyl)-2,4-undecanedione,
8-(3′,5′-dioctyl-4′-hydroxybenzyl)-7,9-pentadecavedione, and the like.

Representative examples of Group II benzylamine compounds include:
N,N-dimethyl, 4-aminomethylphenol;
N,N-dimethyl, 2,6-di-t-butyl-4-aminomethylphenol;
N,N-dimethyl, 2-methyl-6-isopropyl-4-aminomethylphenol;
N,N-dimethyl, 2-methyl-6-t-butyl-4-aminomethylphenol,
N,N-dimethyl, 2,6-diisopropyl-4-aminomethylphenol,
N,N-dimethyl, 2-sec-butyl-4-aminomethylphenol,
N,N-dimethyl, 2-isopropyl-4-aminomethylphenol,
N,N-dimethyl, 2-t-butyl-4-aminomethylphenol,
N,N-diethyl, 2,6-di-t-butyl-4-aminomethylphenol,
N,N-dioctyl, 2,6-di-t-butyl-4-aminomethylphenol,
N,N-dioctyl, 2-ethyl-6-t-butyl-4-aminomethylphenol,
N,N-dioctyl, 2,6-diheptyl-4-aminomethylphenol,
N,N-dioctyl, 2-ethyl-6-methyl-4-aminomethylphenol,
N,N-dioctyl, 2-t-butyl-6-heptyl-4-aminomethylphenol,
N-ethyl,N-methyl, 2,6-di-t-butyl-4-aminomethylphenol,
N-octyl,N-methyl, 2-methyl-6-ethyl-4-aminomethylphenol,
N-(3,5-di-t-butyl-4-hydroxybenzyl)piperidine,
N-(3,5-di-t-butyl-4-hydroxybenzyl)morpholine,
N-(3,5-di-t-butyl-4-hydroxybenzyl)pyrrolidine, and the like.

Representative examples of Group III alkyl halide compounds include:
methyl iodide,
octyl iodide,
methyl bromide,
octyl bromide,
methyl chloride,
octyl chloride,
isopropyl iodide,
isopropyl bromide,
sec-butyliodide,
sec-butylbromide,
3-methyliodobutane, and the like.

Representative examples of Group IV bis(3′,5′-mono or dihydrocarbyl-4′-hydroxybenzyl)-1,3-diketone products which can be prepared by the present process include:
3,3-Bis(3′,5′-di-t-butyl-4′-hydroxybenzyl)-2,4-pentanedione,
3,3-Bis(3′-methyl-5′-isopropyl-4′-hydroxybenzyl)-2,4-pentanedione,
3,3-Bis(3′-methyl-5′-t-butyl-4′-hydroxybenzyl)-2,4-pentanedione,
3,3-Bis(3′,5′-diisopropyl-4′-hydroxybenzyl)-2,4-pentanedione,
3,3-Bis(3′-sec-butyl-4′-hydroxybenzyl)-2,4-pentanedione,
3,3-Bis(3′-isopropyl-4′-hydroxybenzyl)-2,4-pentanedione,
3,3-Bis(3′-t-butyl-4′-hydroxybenzyl)-2,4-pentanedione,
3,3-Bis(3′-ethyl-5′-methyl-4′-hydroxybenzyl)-2,4-heptanedione,
5,5-Bis(3′,5′-dioctyl-4′-hydroxybenzyl)-4,6-nonanedione,
4,4-Bis(3′-t-butyl-5′-heptyl-4′-hydroxybenzyl)-2,6-dimethyl-3,5-heptanedione,
3,3-Bis(3′,5′-dioctyl-4′-hydroxybenzyl)-2,4-decanedione,
3,3-Bis(3′,5′-dioctyl-4′-hydroxybenzyl)-2,4-undecanedione, and
8,8-Bis(3′,5′-dioctyl-4′-hydroxybenzyl)-7,9-pentadecanedione.

In general, the alkaline earth metal halides which may be used in the practice of the present process include the chlorides, bromides and iodides of magnesium, calcium, strontium and barium. Magnesium chloride is preferred.

The process of the invention preferably is carried out by reacting the benzylamine starting material with at least 1 molar equivalent of β-diketone reactant, 1 molar equivalent of alkyl halide reactant and 1 molar equivalent of alkaline earth metal halide although an excess of either or both benzylamine reactant and alkyl halide reactants can be used in order to ensure that the reaction goes to completion. A preferred range of benzylamine reactant to β-diketone reactant is from about 1 to 10 moles of benzylamine per mole of β-diketone. A preferred range of alkyl halide reactant to β-diketone reactant ranges from about 1 to 10 moles of alkyl halide per mole of β-diketone.

At least 1 mole of alkaline earth metal halide per mole of β-diketone reactant should be used in the process of the invention, although an amount of alkaline earth metal halide up to 20 moles of halide per mole of β-diketone reactant can be used, if desired.

The reaction is advantageously carried out with a temperature of about 50° C. to about 500° C. While lower temperatures can be used, the reaction rates are generally correspondingly lower. In any event, operating temperatures which would cause decomposition of the reactants used in the present process or the products produced thereby are to be avoided. Typically, the reaction is conducted at atmospheric pressure. However, higher pressures up to about 1000 psig may be used, if desired. Reflux temperature at atmospheric pressure is effective and preferred.

The use of a solvent for the reaction mixture is not generally required. However, if desired, a solvent which is inert under the reaction conditions, i.e., those solvents which do not enter into the reaction, may be added to the reaction vessel. Useful solvents comprise aprotic solvents which include ethers such as diethyl ether, dibutyl ether, 1-ethoxyhexane, tetrahydrofuran, 1,4-dioxane, 1,3-dioxolane, diglyme, 1,2-diethoxyethane, etc. Especially useful solvents are dipolar aprotic solvents such as dimethyl sulfoxide, N,N-dimethylformamide, N,N-dimethylacetamide, dimethyl sulfone, tetramethylene sulfone, N-methylpyrrolidinone, acetonitrile and like materials. Other solvents which are inert under the reaction conditions may be used: for example, low boiling hydrocarbons, halogenated hydrocarbons, examples of which are benzene, toluene, tetrachloroethane, the chlorinated benzenes, the chlorinated toluenes, etc.

Lower alkanols, preferably those having up to about 6 carbon atoms, also can be used as solvents in the process. These include methanol, ethanol, n-propanol, isopropyl alcohol, n-butanol, sec-butyl alcohol, t-butyl alcohol, n-pentanol, isopentyl alcohol, n-hexanol and isohexyl alcohol.

The amount of solvent can be expressed as a volume ratio of solvent to β-diketone reactant. Suitable volume ratios of solvent to β-diketone reactant can be from about 1/1 to about 500/1 and preferably from about 1/1 to about 300/1.

The mode of addition in the process is not particularly critical. Accordingly, it is convenient to add the benzylamine reactant to a mixture of the other materials, add the β-diketone reactant to a mixture of the other materials, add the alkyl halide reactant to a mixture of the other materials, add the alkaline earth metal halide compound to a mixture of the other materials, add the reactants to a mixture of the benzylamine and solvent, introduce all ingredients simultaneously to the reaction mixture, or the like.

The process should be carried out for the time sufficient to convert substantially all of the β-diketone reactant to the corresponding bis-benzylated 1,3-diketone product. The length of time for optimum yield will depend primarily on the reaction temperature and the particular solvent, if any, used in the reaction. In general, high yields of the bis-benzylated 1,3-diketones are obtained in from about two to about 24 hours.

The process may readily be conducted in a batchwise, semi-batchwise or continuous manner and in conventional equipment.

Under the reaction conditions, the benzylamine reactant is N-alkylated by the alkyl halide reactant to afford a quaternary ammonium salt, which subsequently fragments to give a quinone methide intermediate. This quinone methide intermediate is then alkylated by the 1,3-diketone reactant which is most likely complexed with the metal halide reactant. Attack of the 1,3-diketone on the quinone methide intermediate gives the bis-benzylated product of the present process.

The bis-benzylated 1,3-diketone product is separated from the reaction mixture by such means as distillation, extraction, and other methods obvious to those skilled in the chemical art.

Since the bis-benzylated 1,3-diketone products of the present process are believed to be novel compounds, in a still further embodiment of the present invention, there is provided, as new compositions of matter, compounds of the general formula:

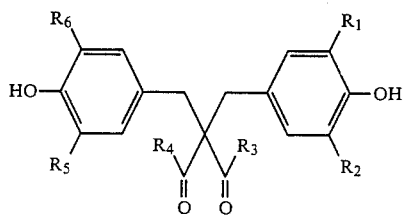

wherein $R_1$, $R_2$, $R_5$ and $R_6$, are the same or different and are hydrogen or hydrocarbyl radicals, preferably alkyl, aralkyl or cycloalkyl radicals having from 1 to about 20 carbon atoms each, and more preferably from 3 to 8 carbon atoms each with the provision that at least one of $R_1$ or $R_2$ and $R_5$ or $R_6$ must be other than hydrogen, and $R_3$, $R_4$, $R_7$ and $R_8$ are the same or different and are hydrocarbyl radicals preferably alkyl, aralkyl or cycloalkyl radicals having from 1 to about 20 carbon atoms, more preferably from 3 to 8 carbon atoms each.

The bis-benzylated 1,3-diketone products prepared by the process of this invention have antioxidant properties and are capable of stabilizing polymers normally subject to oxidative degradation when incorporated into the polymers using conventional techniques such as by addition to polymer lattices; or by addition to solid polymers on a mill or in a Banbury. Further, the novel compounds of this invention are deemed effective as antioxidants in both unleaded and leaded gasolines made from a wide variety of base stocks and for engine and industrial oils which are derived from crude petroleum or produced synthetically.

The practice of this invention will be still further apparent by the following illustrative examples.

EXAMPLE I

Bis(3',5-di-t-butyl-4'-hydroxybenzyl)acetylacetone

Into a 25 mL glass reaction vessel, an ethanol solution (7 mLs) of N,N-dimethyl, 2,6-di-t-butyl-4-aminomethylphenol (0.47 g, 1.8 mmol) was treated with methyl iodide (0.25 g, 1.8 mmol) and then stirred at room temperature for several minutes. In a separate 100 mL glass reaction vessel, an ethanol solution (15 mLs) of 3',5'-di-t-butyl-4'-hydroxybenzylacetylacetone (0.58 g, 1.8 mmol) was treated with magnesium chloride (0.17 g, 1.8 mmol). Next, the ethanol solution which contained the 3',5'-di-t-butyl-4'-hydroxybenzylacetylacetone and magnesium chloride was added to the ethanol solution containing the quaternary salt derived from N,N-dimethyl,2,6-di-t-butyl-4-aminomethylphenol and methyl iodide. The reaction mixture was stirred at room temperature for 45 minutes. Water (~2 mLs) and a small amount of triethylamine was added and the reaction mixture was refluxed for 1 hour. Upon cooling the reaction mixture, a crystalline product (0.6 g) which was shown by NMR to be bis(3',5'-di-t-butyl-4'-hydroxybenzyl)acetylacetone, was collected (62%).

Having disclosed the process of the present invention, one skilled in the art can readily envision various modifications and changes which are nevertheless within the scope of the invention. Therefore, it is desired that the process of this invention be limited only by the lawful scope of the appended claims.

We claim:

1. A process for the preparation of bis(3',5'-mono or dihydrocarbyl-4'-hydroxybenzyl)-1,3-diketones having the general structural formula:

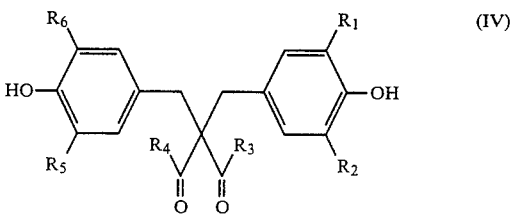

(IV)

which comprises reacting a (3',5'-mono or dihydrocarbyl-4'-hydroxybenzyl)-1,3-diketone of the general structural formula:

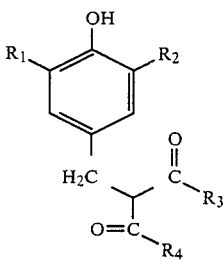

(I)

with an N,N-dihydrocarbyl-2,6-mono or dihydrocarbyl-4-aminomethylphenol of the general structural formula:

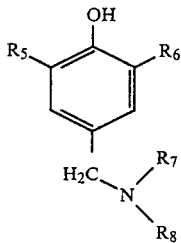

(II)

and an alkyl halide of the general formula $R_9X$        (III)

in the presence of an alkaline earth metal halide wherein $R_1$, $R_2$, $R_5$ and $R_6$, are the same or different and are hydrogen or hydrocarbyl radicals, with the provision that at least one of $R_1$ or $R_2$ and $R_5$ or $R_6$ must be other than hydrogen, $R_3$, $R_4$, $R_7$ and $R_8$ are the same or different and are hydrocarbyl radicals, and $R_9$ is a linear or branched alkyl radical having from 1 to about 20 carbon atoms and X is bromine, chlorine or iodine.

2. The process of claim 1 wherein said hydrocarbyl radicals are linear or branched alkyl, aralkyl or cycloalkyl radicals having from 1 to about 20 carbons atoms each.

3. The process of claim 1 wherein said alkaline earth metal halide is selected from the chlorides, bromides or iodides of magnesium, calcium, strontium and barium.

4. The process of claim 1 wherein compounds having the general structural formula (I) are
3-(3',5'-di-t-butyl-4'-hydroxybenzyl)-2,4-pentanedione,
3-(3'-methyl-5'-isopropyl-4'-hydroxybenzyl)-2,4-pentanedione,
3-(3'-methyl-5'-t-butyl-4'-hydroxybenzyl)-2,4-pentanedione,
3-(3',5'-diisopropyl-4'-hydroxybenzyl)-2,4-pentanedione,
3-(3'-sec-butyl-4'-hydroxybenzyl)-2,4-pentanedione,
3-(3'-isopropyl-4'-hydroxybenzyl)-2,4-pentanedione,
3-(3'-t-butyl-4'-hydroxybenzyl)-2,4-pentanedione,
3-(3'-ethyl-5'-methyl-4'-hydroxybenzyl)-2,4-heptanedione,
5-(3',5'-dioctyl-4'-hydroxybenzyl)-4,6-nonanedione,
4-(3'-t-butyl-5'-heptyl-4'-hydroxybenzyl)-2,6-dimethyl-3,5-heptanedione,
3-(3',5'-dioctyl-4'-hydroxybenzyl)-2,4-decanedione
3-(3',5'-dioctyl-4'-hydroxybenzyl)-2,4-undecanedione, or
8-(3',5'-dioctyl-4'-hydroxybenzyl)-7,9-pentanedione.

5. The process of claim 1 wherein compounds having the general structural formula (II) are
N,N-dimethyl,4-aminomethylphenol;
N,N-dimethyl,2,6-di-t-butyl-4-aminomethylphenol;
N,N-dimethyl,2-methyl-6-isopropyl-4-aminomethylphenol;
N,N-dimethyl,1,2-methyl-6-t-butyl-4-aminomethylphenol,
N,N-dimethyl,1,2,6-diisopropyl-4-aminomethylphenol,
N,N-dimethyl,1,2-sec-butyl-4-aminomethylphenol,
N,N-dimethyl,1,2-isopropyl-4-aminomethylphenol,
N,N-dimethyl,1,2-t-butyl-4-aminomethylphenol,
N,N-diethyl,1,2,6-di-t-butyl-4-aminomethylphenol,
N,N-dioctyl,1,2,6-di-t-butyl-4-aminomethylphenol,
N,N-dioctyl,1,2-ethyl-6-t-butyl-4-aminomethylphenol,
N,N-dioctyl,1,2,6-diheptyl-4-aminomethylphenol,
N,N-dioctyl,1,2-ethyl-6-methyl-4-aminomethylphenol,
N,N-dioctyl,1,2-t-butyl-6-heptyl-4-aminomethylphenol,
N-ethyl,N-1,methyl,2,6-di-t-butyl-4-aminomethylphenol,
N-octyl,N-methyl,2-methyl-6-ethyl-4-aminomethylphenol,
N-(3,5-di-t-butyl-4-hydroxybenzyl)piperidine,
N-(3,5-di-t-butyl-4-hydroxybenzyl)morpholine, or
N-(3,5-di-t-butyl-4-hydroxybenzyl)pyrrolidine.

6. The process of claim 1 wherein the compounds of the general structural formula (III) are
methyl iodide,
octyl iodide,
methyl bromide,
octyl bromide,
methyl chloride,
octyl chloride,
isopropyl iodide,
isopropyl bromide,
sec-butyliodide,
sec-butylbromide, or
3-methyliodobutane.

7. The process of claim 1 wherein the compound produced by the process is 3,3-bis(3', 5'-di-t-butyl-4'-hydroxybenzyl)-2,4-pentanedione.

8. the process of claim 1 wherein the compound produced by the process is 3,3-bis(3'-methyl-5'-isopropyl-4'-hydroxybenzyl)-2,4-pentanedione.

9. The process of claim 1 wherein the compound produced by the process is 3,3-bis(3'-methyl-5'-t-butyl-4'-hydroxybenzyl)-2,4-pentanedione.

10. The process of claim 1 wherein the compound produced by the process is 3,3-bis(3', 5'-diisopropyl-4'-hydroxybenzyl)-2,4-pentanedione.

11. The process of claim 1 wherein the compound produced by the process is 3,3-bis(3'-sec-butyl-4'-hydroxybenzyl)-2,4-pentanedione.

12. The process of claim 1 wherein the compound produced by the process is 3,3-bis(3'-isopropyl-4'-hydroxybenzyl)-2,4-pentanedione.

13. The process of claim 1 wherein the compound produced by the process is 3,3-bis(3'-t-butyl-4'-hydroxybenzyl)2,4-pentanedione.

14. The process of claim 1 wherein the compound produced by the process is 3,3-bis(3'-ethyl-5'-methyl-4'-hydroxybenzyl)-2,4-heptanedione.

15. The process of claim 1 wherein the compound produced by the process is 5,5-bis(3', 5'-dioctyl-4'-hydroxybenzyl)-4,6-nonanedione.

16. The process of claim 1 wherein the compound produced by the process is 4,4-bis(3'-t-butyl-5'-heptyl-4'-hydroxybenzyl)-2,6-dimethyl-3,5-heptanedione.

17. The process of claim 1 wherein the compound produced by the process is 3,3-bis(3', 5'-dioctyl-4'-hydroxybenzyl)-2,4-decanedione.

18. The process of claim 1 wherein the compound produced by the process is 3,3-bis(3',5'-dioctyl-4'-hydroxybenzyl)-2,4-undecanedione.

19. The process of claim 1 wherein the compound produced by the process is 8,8-bis(3',5'-dioctyl-4'-hydroxybenzyl)-7,9-pentadecanedione.

20. The process of claim 1 wherein the molar ratio of benzylamine reactant to β-diketone reactant is from about 1 to 10 moles of benzylamine per mole of β-diketone.

21. The process of claim 1 wherein the molar ratio of alkyl halide reactant to β-diketone reactant is from about 1 to 10 moles of alkyl halide per mole of β-diketone.

22. The process of claim 1 wherein said reaction is conducted at elevated temperature.

23. The process of claim 22 wherein the reaction is carried out at a temperature of about 50° C. to about 500° C.

24. The process of claim 1 wherein said reaction is carried out under pressure in the range of about atmospheric to about 1000 psig.

25. The process of claim 1 wherein said reaction is carried out in the temperature range of about 50° C. to 500° C. and under pressure in the range of from about atmospheric to about 1000 psig.

26. The process of claim 1 wherein said reaction is carried out in the presence of a solvent which is inert under the reaction conditions.

27. The process of claim 26 wherein said solvent is an aprotic solvent.

28. The process of claim 27 wherein said aprotic solvent is a dipolar aprotic solvent.

29. The process of claim 28 wherein said dipolar aprotic solvent is selected from dimethylsulfoxide, N,N-dimethylformamide, N,N-dimethylacetamide, dimethylsulfone, tetramethylenesulfone, N-methylpyrrolidinone and acetonitrile.

30. The process of claim 26 wherein said solvent is a lower alkanol having from 1 to about 6 carbon atoms.

31. The process of claim 26 wherein the volume ratio of solvent to β-diketone reactant is from about 0/1 to about 500/1.

32. The process of claim 1 wherein said hydrocarbyl radicals are linear or branched alkyl, aralkyl or cycloalkyl radicals containing from 3 to 8 carbon atoms.

* * * * *

UNITED STATES PATENT AND TRADEMARK OFFICE
CERTIFICATE OF CORRECTION

PATENT NO. : 4,532,356

DATED : July 30, 1985

INVENTOR(S) : Charles R. Everly et al.

It is certified that error appears in the above-identified patent and that said Letters Patent is hereby corrected as shown below:

Column 2, line 27, " 3',5 " should read -- 3',5' --;

Column 6, line 22, " 3',5 " should read -- 3',5' --;

Column 8, line 7, " N,N-dimethyl,1,2- " should read -- N,N-dimethyl,2- --;

Column 8, line 9, " N,N-dimethyl,1,2,6- " should read -- N,N-dimethyl,2,6- --;

Column 8, line 10, " N,N-dimethyl,1,2- " should read -- N,N-dimethyl,2- --;

Column 8, line 11, " N,N-dimethyl,1,2- " should read -- N,N-dimethyl,2- --;

Column 8, line 12, " N,N-dimethyl,1,2- " should read -- N,N-dimethyl,2- --;

Column 8, line 13, " N,N-diethyl,1,2,6- " should read -- N,N-diethyl,2,6- --;

Column 8, line 14, " N,N-dioctyl,1,2,6- " should read -- N,N-dioctyl,2,6- --;

Column 8, line 15, " N,N-dioctyl,1,2- " should read -- N,N-dioctyl,2- --;

Column 8, line 16, " N,N-dioctyl,1,2,6- " should read -- N,N-dioctyl,2,6- --;

UNITED STATES PATENT AND TRADEMARK OFFICE
CERTIFICATE OF CORRECTION

PATENT NO. : 4,532,356
DATED : July 30, 1985
INVENTOR(S) : Charles R. Everly et al.

It is certified that error appears in the above-identified patent and that said Letters Patent is hereby corrected as shown below:

Column 8, line 17, " N,N-dioctyl,1,2- " should read
-- N,N-dioctyl,2- --;

Column 8, line 18, " N,N-dioctyl,1,2- " should read
-- N,N-dioctyl,2- --;

Column 8, line 19, " N-ethyl,N-1,methyl " should read
-- N-ethyl,N-methyl --;

Column 8, line 42, " the " should read -- The --.

Signed and Sealed this

Nineteenth Day of November 1985

[SEAL]

Attest:

Attesting Officer

DONALD J. QUIGG

Commissioner of Patents and Trademarks